(12) United States Patent
Halmann et al.

(10) Patent No.: US 9,561,015 B2
(45) Date of Patent: Feb. 7, 2017

(54) METHOD AND APPARATUS FOR VOICE RECORDING WITH ULTRASOUND IMAGING

(75) Inventors: Menachem Halmann, Milwaukee, WI (US); David J. Bates, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1612 days.

(21) Appl. No.: 11/895,315

(22) Filed: Aug. 24, 2007

(65) Prior Publication Data

US 2009/0054768 A1 Feb. 26, 2009

(51) Int. Cl.
*A61B 8/00* (2006.01)

(52) U.S. Cl.
CPC *A61B 8/00* (2013.01); *A61B 8/468* (2013.01)

(58) Field of Classification Search
CPC .................................. A61B 8/00; A61B 8/468
USPC .................. 600/300, 437, 443, 447; 707/821
See application file for complete search history.

(56) References Cited

U.S. PATENT DOCUMENTS

| | | | | |
|---|---|---|---|---|
| 6,237,010 B1 * | 5/2001 | Hui et al. | | 715/205 |
| 6,384,861 B1 * | 5/2002 | Lindsey | | 348/169 |
| 6,569,097 B1 | 5/2003 | McMorrow et al. | | |
| 6,774,939 B1 * | 8/2004 | Peng | | 348/231.4 |
| 7,287,088 B1 * | 10/2007 | Anderson | | 709/235 |
| 7,436,408 B2 * | 10/2008 | Hayashi et al. | | 345/473 |
| 2003/0083577 A1 * | 5/2003 | Greenberg | | 600/437 |
| 2004/0125143 A1 * | 7/2004 | Deaton et al. | | 345/765 |
| 2004/0268413 A1 * | 12/2004 | Reid et al. | | 725/131 |
| 2006/0226298 A1 * | 10/2006 | Pierson | | 246/1 R |

FOREIGN PATENT DOCUMENTS

| | | |
|---|---|---|
| JP | 03-071264 A | 3/1991 |
| JP | 2005-117260 A | 4/2005 |
| JP | 2006-141466 A | 6/2006 |

OTHER PUBLICATIONS

Unofficial translation of Japanese Patent Office Action for JP Application No. 2008-213416 dated Sep. 10, 2013.

* cited by examiner

*Primary Examiner* — Michael Rozanski
(74) *Attorney, Agent, or Firm* — Dean D. Small; The Small Patent Law Group, LLC.

(57) ABSTRACT

An ultrasound system comprises a probe for acquiring ultrasound data associated with a patient and a microphone detecting audio. The system further comprises a processor module and a memory. The processor module is configured to receive the ultrasound data from the probe and processes the ultrasound data to form an image file. The processor module is further configured to receive the audio from the microphone and forms a voice recording file based on the received audio. The memory stores the image file and the voice recording file, and the processor module automatically associates the image file and the voice recording file with each other.

17 Claims, 7 Drawing Sheets

METHOD AND APPARATUS FOR VOICE RECORDING WITH ULTRASOUND IMAGING

BACKGROUND OF THE INVENTION

This invention relates generally to ultrasound imaging, and more particularly, to recording vocal information during an ultrasound exam.

Ultrasound systems are finding use in an increasing number of applications. The cost of an ultrasound exam may be less than other technologies, and the portability of the system provides many advantages. Cart-based systems are often used in hospital and clinic settings, but smaller sized systems, such as laptop computer, pocket and handheld systems are becoming more popular due to their portability as well as lower cost.

Regardless of the size of the ultrasound system, ultrasound exams can be complicated and time consuming. An operator, such as a physician and/or sonographer often wishes to record notes, findings, observations, diagnosis and the like during the exam, often directed to a particular image or series of images. For a system that provides a keyboard, the operator either types with one hand while scanning with the other, or has to remove the scanning probe from the patient. In some cases, such as during surgery or an interventional or invasive procedure, the operator may not be able to access the unit to enter comments. While scanning with a smaller handheld system, the operator may hold the unit in one hand and the probe in the other. Therefore, keyboard entry, if even provided, is difficult or impossible to accomplish without disrupting the procedure. In order to make any permanent record, the operator relies on memory and records a diagnosis after the exam is complete or must stop scanning in order to write or otherwise record notes.

Therefore, a need exists for a hands-free ability to record findings and comments during an ultrasound procedure.

BRIEF DESCRIPTION OF THE INVENTION

In one embodiment, an ultrasound system comprises a probe for acquiring ultrasound data associated with a patient and a microphone detecting audio. The system further comprises a processor module and a memory. The processor module is configured to receive the ultrasound data from the probe and processes the ultrasound data to form an image file. The processor module is further configured to receive the audio from the microphone and form a voice recording file based on the received audio. The memory stores the image file and the voice recording file, and the processor module automatically associates the image file and the voice recording file with each other.

In another embodiment, a method for recording audio associated with an ultrasound image file comprises acquiring ultrasound data from a probe. An image file is stored based on the ultrasound data. A voice recording file is digitally recorded, and the image file and the voice recording file are automatically associated with each other when storing the voice recording file.

In yet another embodiment, an ultrasound system comprises a probe for acquiring ultrasound data. A display displays the ultrasound data and a microphone detects audio. A processor module is configured to form an image file based on the ultrasound data. The processor module is configured to receive the audio from the microphone and forms a voice recording file that is associated with the image file. The voice recording file is based on the audio.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
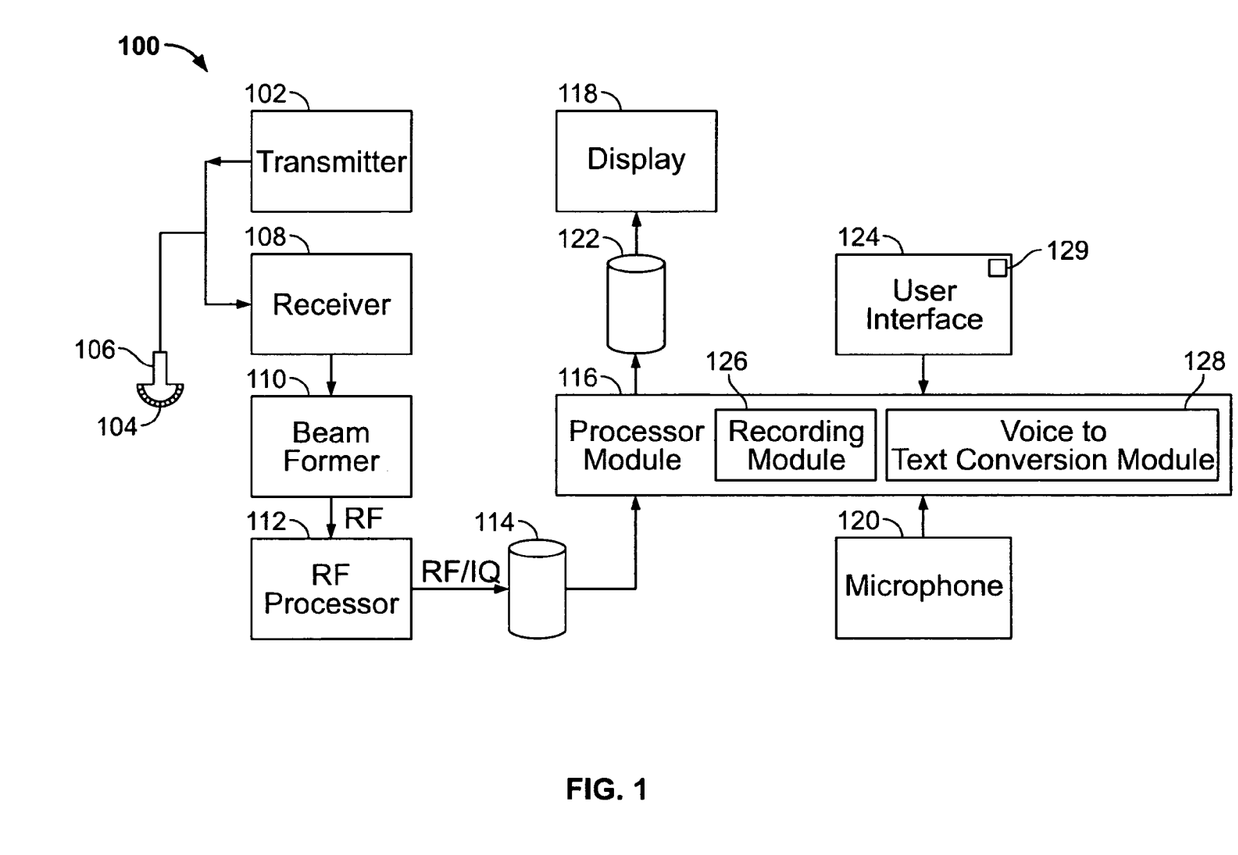
FIG. 1 is a block diagram of an ultrasound system formed in accordance with an embodiment of the present invention.

FIG. 1 is a block diagram of an ultrasound system 100 including a transmitter 102 that drives an array of elements 104 (e.g., piezoelectric elements) within a probe 106 to emit pulsed ultrasonic signals into a body. A variety of geometries may be used. Each probe 106 has a defined center operating frequency and bandwidth. The ultrasonic signals are back-scattered from structures in the body, like blood cells or muscular tissue, to produce echoes that return to the elements 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to a memory 114 for storage.

The ultrasound system 100 also includes a processor module 116 to process the acquired ultrasound information (e.g., RF signal data or IQ data pairs) and prepare frames of ultrasound information for display on display 118. The processor module 116 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 during a scanning session and then processed and displayed in an off-line operation.

The processor module 116 is connected to a user interface 124 that may control operation of the processor module 116 as explained below in more detail. The functionality within the processor module 116 may be provided by hardware, software, or any combination of hardware and software. The processor module 116 also has a recording module 126 that receives audio from a microphone 120. The microphone 120 is provided for recording voice information during the exam that is associated with an image currently being acquired and/or previously acquired. An audio recording control interface 129 may be provided on the user interface 124 to activate and/or deactivate the microphone 120 and recording module 126 to facilitate starting and/or stopping of a recording session after which a voice recording file is stored in memory 122, which may be stored automatically or after a user confirmation.

A voice to text conversion module 128 may be provided to convert the digital voice recording file to written text. The voice to text conversion may also be accomplished on other systems, such as a laptop or review station. The voice to text conversion module 128 may produce a written transcript that may be associated with a particular image file and/or patient file, or may be used to populate a report page associated with the patient. In one example, the voice to text conversion module 128 may convert the associated voice recording file to text that is displayed within or linked to a diagnosis section, such as beneath the associated image displayed on the display 118 or indicated by an icon superimposed on the image (as described in further detail below).

The display 118 includes one or more monitors that present patient information, including diagnostic ultrasound images to the user for diagnosis and analysis. One or both of memory 114 and memory 122 may store three-dimensional data sets of the ultrasound data, where such three-dimensional (3D) data sets are accessed to present two-dimensional (2D) and 3D images. The images may be modified and the display settings of the display 118 may be manually adjusted using the user interface 124.

Figure 2:
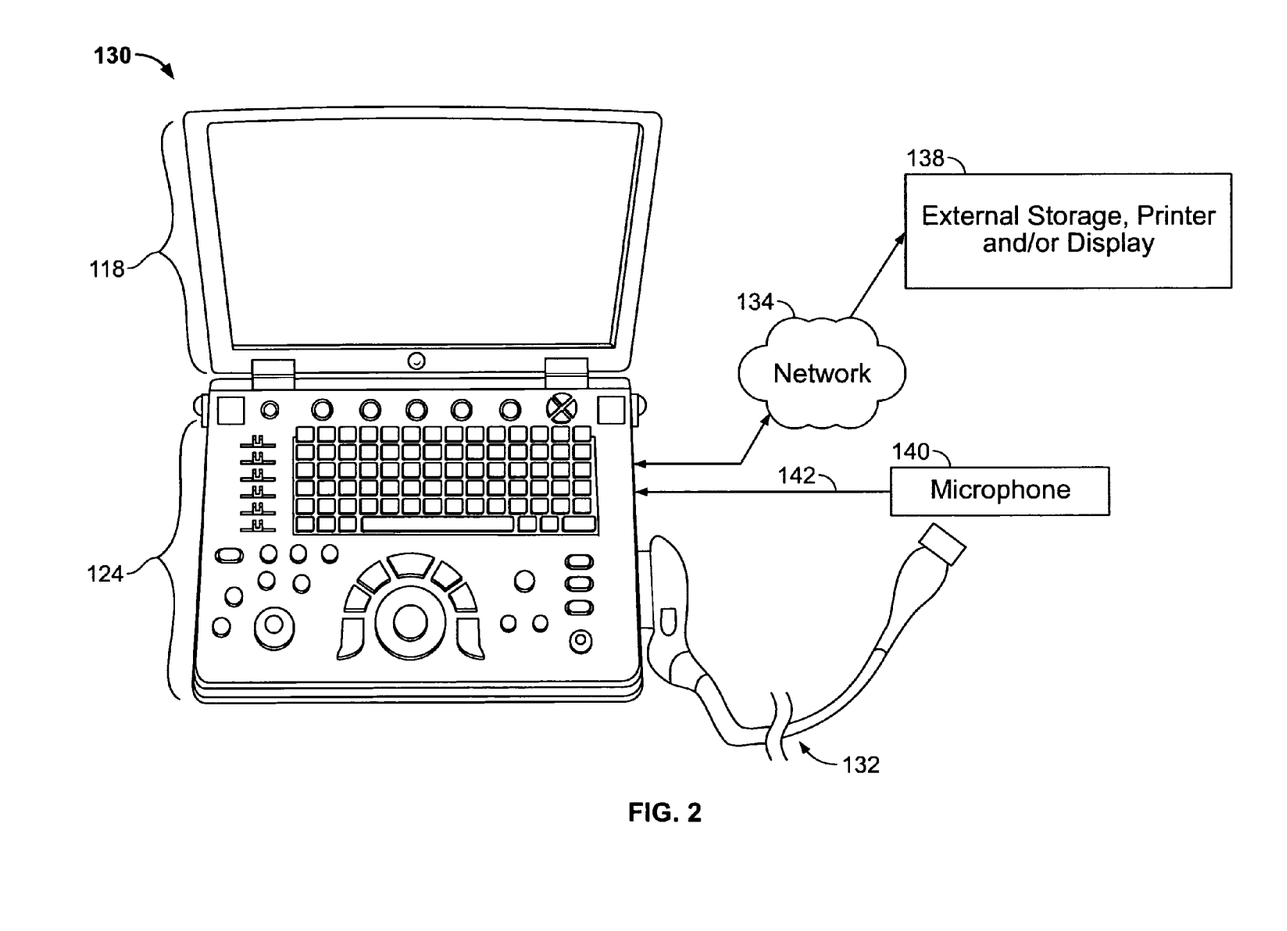
FIG. 2 illustrates a 3D-capable miniaturized ultrasound system formed in accordance with an embodiment of the present invention.
Figure 3:
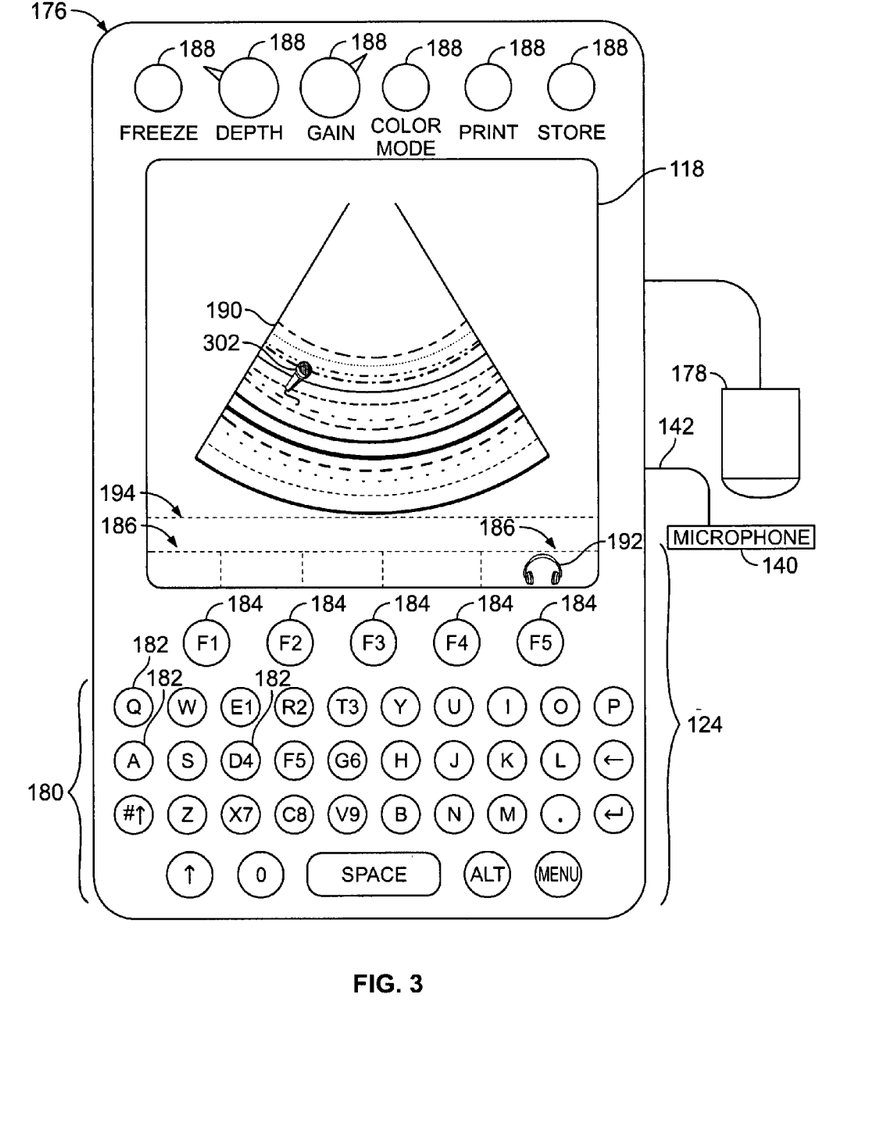
FIG. 3 illustrates a hand carried or pocket-sized ultrasound imaging system formed in accordance with an embodiment of the present invention.
Figure 4:
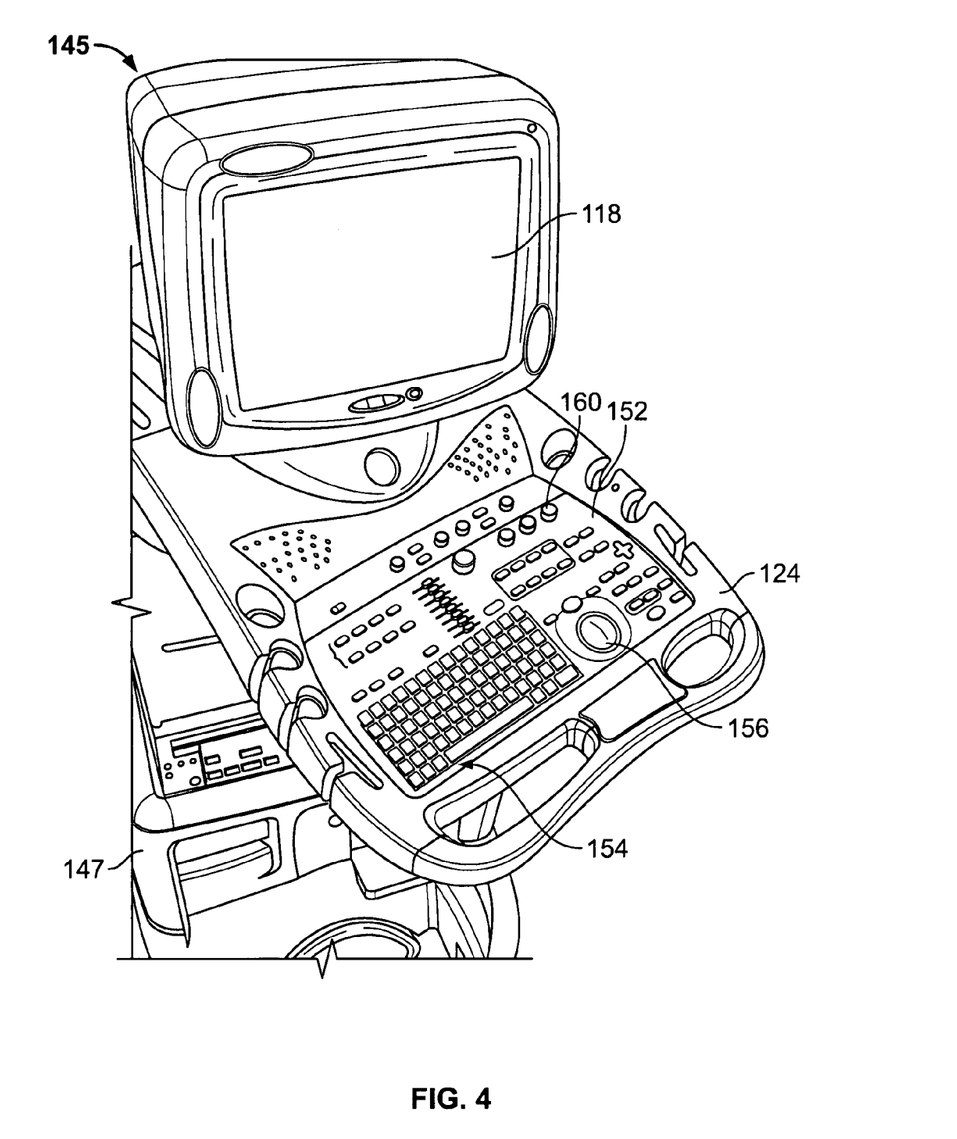
FIG. 4 illustrates a portable ultrasound imaging system formed in accordance with an embodiment of the present invention.

The generalized ultrasound system 100 of FIG. 1 may be embodied in a small-sized system, such as laptop computer or pocket sized system as well as in a larger cart-based system. FIGS. 2 and 3 are directed towards small-sized systems, while FIG. 4 is directed towards larger systems.

FIG. 2 illustrates a 3D-capable miniaturized ultrasound system 130 having a probe 132 that may be configured to acquire 3D ultrasonic data. For example, the probe 132 may have a 2D array of elements 104 as discussed previously with respect to the probe 106 of FIG. 1. A user interface 124 (that may also include an integrated display 118) is provided to receive commands from an operator. As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer, for instance, having dimensions of approximately 2.5 inches in depth, approximately 14 inches in width, and approximately 12 inches in height. The ultrasound system 130 may weigh about ten pounds, and thus is easily portable by the operator. The integrated display 118 (e.g., an internal display) is also provided and is configured to display a medical image.

The ultrasonic data may be sent to an external device 138 via a wired or wireless network 134 (or direct connection, for example, via a serial or parallel cable or USB port). In some embodiments, external device 138 may be a computer or a workstation having a display. Alternatively, external device 138 may be a separate external display or a printer capable of receiving image data from the hand carried ultrasound system 130 and of displaying or printing images that may have greater resolution than the integrated display 118.

A microphone 140 may be provided separate from or integral with the ultrasound system 130. The microphone 140 may be any known audio pick-up device. For example, the microphone 140 may be a desk stand model, extending substantially perpendicular from a base configured to rest on a flat surface. Alternatively, the microphone 140 may be configured with a clip such as to attach to an operator's collar or other clothing to be positioned near the operator's mouth. Communication link 142 may be a hard-wired link between the microphone 140 and system 130, or may be wireless, communicating, for example, over infrared or radio waves.

FIG. 3 illustrates a hand carried or pocket-sized ultrasound imaging system 176 wherein the display 118 and user interface 124 form a single unit. By way of example, the pocket-sized ultrasound imaging system 176 may be a pocket-sized or hand-sized ultrasound system approximately 2 inches wide, approximately 4 inches in length, and approximately 0.5 inches in depth and weighs less than 3 ounces. The pocket-sized ultrasound imaging system 176 generally includes the display 118 and user interface 124, which may or may not include a keyboard-type interface and an input/output (I/O) port for connection to a scanning device, for example, an ultrasound probe 178. The display 118 may be, for example, a 320×320 pixel color LCD display (on which a medical image 190 may be displayed). A typewriter-like keyboard 180 of buttons 182 may optionally be included in the user interface 124.

Multi-function controls 184 may each be assigned functions in accordance with the mode of system operation. Therefore, each of the multi-function controls 184 may be configured to provide a plurality of different actions. Label display areas 186 associated with the multi-function controls 184 may be included as necessary on the display 118. The system 176 may also have additional keys and/or controls 188 for special purpose functions, which may include, but are not limited to "freeze," "depth control," "gain control," "color-mode," "print," and "store."

The microphone 140 and communication link 142 are also shown. One of the label display areas 186 may display a recording icon 192 associated with audio recording, indicating that recording capability is available and/or that the recording capability is active or not active. The recording icon 192 may be any representation and may be configurable by the operator. The recording icon 192 may also change based on the state of recording. A first color may be used to indicate an ON state of recording while a second different color is used to indicate an OFF state of recording. Alternatively, separate, different icons (not shown) may be used to indicate activated (ON state) and deactivated (OFF state) recording status. The control of the recording may be provided through the associated multi-function control 184. For example, recording may be activated and deactivated by selecting multi-function control F5 as shown in FIG. 3. Additionally, audio recordings may be associated with particular location(s) on the image 190, as shown by recording icon 302 displayed on the image 190 and as discussed further below.

The display 118 may also have a textual display area 194. After the user records an audio recording, the voice to text conversion module 128 may convert the audio recording to text that is displayed within the textual display area 194 concurrently with the associated diagnostic image.

It should be noted that the various embodiments may be implemented in connection with miniaturized or small-sized ultrasound systems having different dimensions, weights, and power consumption. For example, the pocket-sized ultrasound imaging system 176 and the miniaturized ultrasound system 130 of FIG. 2 may provide the same scanning and processing functionality as the system 100 (shown in FIG. 1).

FIG. 4 illustrates a portable ultrasound imaging system 145 provided on a movable base 147. The portable ultrasound imaging system 145 may also be referred to as a cart-based system. A display 118 and user interface 124 are provided and it should be understood that the display 118 may be separate or separable from the user interface 124. The user interface 124 may optionally be a touchscreen, allowing the operator to select options by touching displayed graphics, icons, and the like.

The user interface 124 also includes control buttons 152 that may be used to control the portable ultrasound imaging system 145 as desired or needed, and/or as typically provided. The user interface 124 provides multiple interface options that the user may physically manipulate to interact with ultrasound data and other data that may be displayed, as well as to input information and set and change scanning parameters. An audio recording control interface 160 and an attached or detached microphone (not shown) are provided as previously discussed. The interface options may be used for specific inputs, programmable inputs, contextual inputs, and the like. For example, a keyboard 154 and track ball 156 may be provided.

Figure 5:
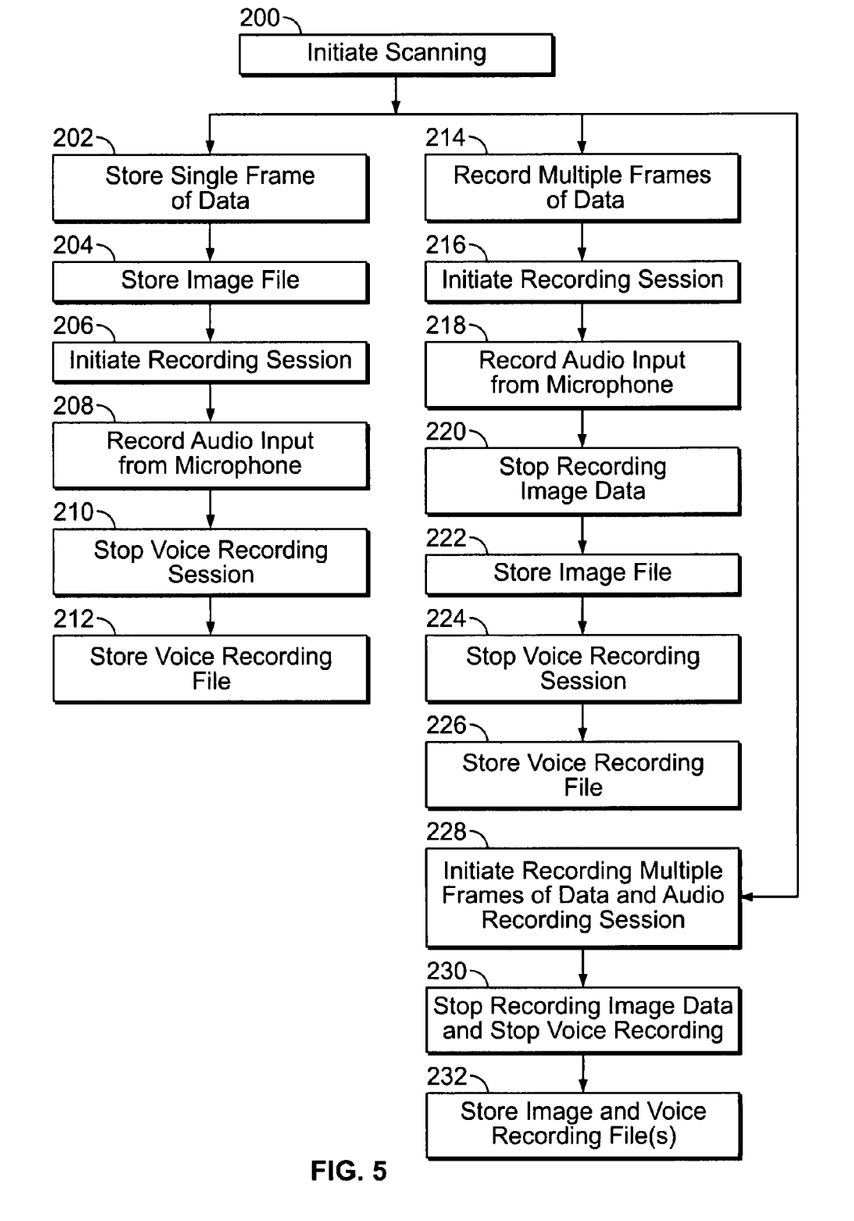
FIG. 5 illustrates a method for acquiring digital voice recording and ultrasound image files and associating the files with each other in accordance with an embodiment of the present invention.

FIG. 5 illustrates a method for acquiring and associating a digital voice recording file and an ultrasound image file. By being able to record one or more digital voice recording files during an exam, the operator does not have to stop scanning to record findings, comments, notes and the like manually and does not have to take extra time that may be needed to enter findings with one hand via a keyboard. Also, an ultrasound system may not have a keyboard, and thus a voice recording file can be entered by the operator at the time of the acquisition. This may allow additional information to be recorded about the patient that may be pertinent to a particular image without the operator having to enter detailed notes manually into a patient's file. Also, during some procedures, such as a biopsy, it may not be possible to stop the exam in order to record findings, and the concurrent voice recording ability allows the operator to easily record the findings quickly and without having to stop scanning.

At 200, an operator initiates scanning of a patient. The operator may select a predefined protocol or may enter parameters manually by selecting one or more buttons on the user interface 124. The operator may scan for a period of time until locating or forming an image that is to be recorded in the memory 122. For example, a single frame of data or a snapshot may be recorded or multiple frames of data may be recorded. An example of multiple frames of data is a cine-loop or movie-clip type of file.

Figure 6:
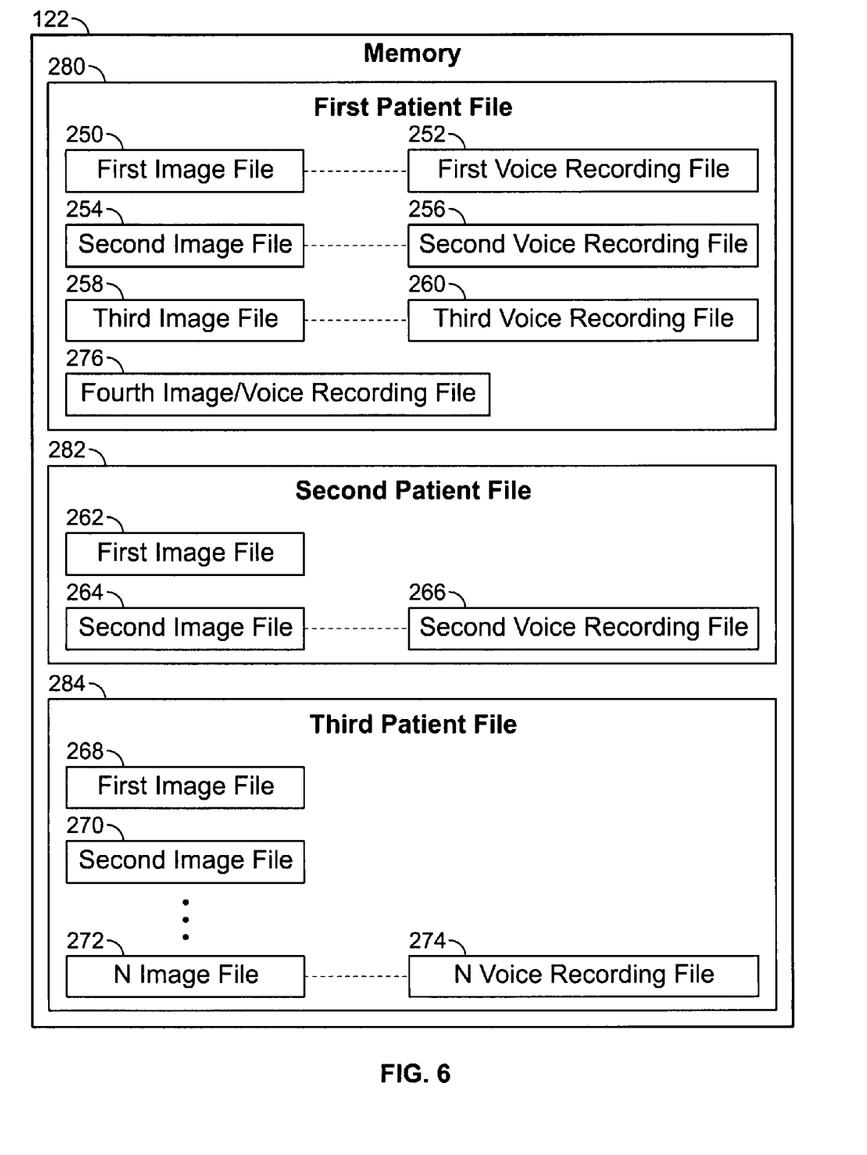
FIG. 6 illustrates associated voice recording and image files stored within a memory in accordance with an embodiment of the present invention.

In one embodiment, at 202 the operator may select a button to store a single frame of image data. At 204, the processor module 116 stores the frame of data, such as in an ultrasound image file in the memory 122. FIG. 6 illustrates files stored within the memory 122 of FIG. 1. The files may be stored in a database format or other known format. Typically, the files are organized such that all files associated with a patient and/or a particular scanning session of the patient are stored or linked together. Returning to 204 of FIG. 5, the processor module 116 may store a first frame of data as first image file 250 within First Patient File 280. The first image file 250 may be any known file storage format, such a jpg, DICOM and the like.

At 206, the operator may initiate a recording session, such as by pushing or activating the audio recording control interface 129 on the user interface 124. In this example, when the recording session is initiated, the processor module 116 associates the resultant voice recording file with the last stored image file. Therefore, the operator may acquire and store a plurality of ultrasound image files, and when the recording session is initiated, the recording session is associated with the last stored image file in the plurality of ultrasound image files. In another embodiment, the operator may select or identify a different image to associate the voice recording file with that is not the last stored image file. The associated image file may be stored prior to or subsequent to acquisition of the voice recording file.

The operator may use the microphone 120, which may be provided on the system or may be separate from the system, such as a clip-on audio pick-up device, to record audio. The processor module 116 activates the recording module 126, and at 208, audio such as voice and other sound detected by the microphone 120 is recorded. For example, the operator may wish to verbally record findings and analysis related to the first image file 250. The operator may also wish to record data that may be used to annotate the recorded image, such as identification of the imaged anatomy. The operator may also wish to verbally input data associated with the first image file 250 that will be used to populate a report page or annotate an image associated with the first image file 250.

At 210, the operator stops the recording session, such as by pressing the audio recording control interface 129 again. At 212, the processor module 116 may store a digital voice recording file in the memory 122 as first voice recording file 252. The first voice recording file 252 may be stored in any known audio-capable digital file storage format such as "wav", "MP3", "MP4" and the like. The first voice recording file 252 is logically associated with the first image file 250, that is, the processor module 116 forms a digital link between the two files. The files may be similarly named, such as first file, or may be named based on the type of scan being acquired, such as second cardiac file, third cardiac file and the like, but have a different extension indicating the type of storage format. For example, the extension of the image file may be "jpg" while the extension of the voice recording is "MP3", based on the particular file storage format. Alternatively, both the image file and voice recording may be stored as "MP3" or "MP4". It should be understood that other types of naming conventions, extensions and file storage formats may be used.

Returning to 200, in another embodiment multiple frames of data, such as a cine-loop or movie, may be desired. At 214, the operator may select a button to begin recording a series of frames of data. One common type of scan is a cine-loop that acquires one or more cardiac cycles. The acquisition therefore varies in length of time, and may be several seconds long or longer, such as when scanning a fetus.

At 216, the operator may initiate a recording session, and at 218 the recording module 126 records an audio recording as detected by the microphone 120. The audio recording may therefore overlap in time with the acquisition of the image file. At 220 the operator may stop recording image data and at 222, the processor module 116 stores the ultrasound image file, such as in second image file 254. At 224 the operator stops the audio recording session, and at 226 the processor module 116 stores the audio recording as second voice recording file 256. The second image file 254 and the second voice recording file 256 are associated with each other.

It should be understood that the length of the image file time t1 and the voice recording file time t2 may be different. For example, the image file time t1 may be 3 or 5 seconds, while the voice recording file time t2 is 60 seconds. Also, the voice recording may be stopped prior to the image recording, resulting in a relatively shorter voice recording file time t2. In another embodiment, the operator may choose to record the cine-loop prior to initiating the voice recording. For example, the operator may watch the recorded cine-loop playing on the display 118 while recording the voice recording file.

In yet another embodiment, at 228 the operator may select an option that initiates recording multiple frames of image data simultaneously with an audio recording session. In this example, the voice recording file time t2 is the same as the image file time t1. If the operator is scanning over a longer period of time, this option may allow the operator to verbally identify select landmarks and other points of interest in the image file as the landmarks are displayed. If desired, the operator can also record movements of a cursor or other visible on-screen tool (e.g., a measurement indicator) synchronized with the audio recording so that when the audio recording is played back, the image file with movements of the cursor or other on-screen tool is replayed. In other words, the image file and the voice recording file (and optionally on-screen cursor or other tool movements) are synchronized with respect to each other. At 230, the operator stops the image and voice recording, and at 232 the processor module 116 stores a third image file 258 and a third voice recording file 260. The two files are associated with each other as discussed previously. Alternatively, a single combined file, such as fourth image/voice recording file 276 may be created and stored using technology that supports both video and audio, such as MP3 or MP4. The fourth image/voice recording file 276 may combine the ultrasound images with the voice recording in a single synchronized file.

In some embodiments, the image file may include stereo sound, such as when scanning in Spectral Doppler mode. In this example, the third image file 258 may have both the ultrasound image data as well as audio that is other than voice, and may also be associated with the third voice recording file 260. Alternatively, when scanning to acquire both image data and audio, a single combined file including voice data may be stored. For example, the fourth image/voice recording file 276 may include image data and audio, such as associated with Doppler scanning, as well as voice recording that is synchronized with the image data.

In yet another embodiment, the processor module 116 may monitor input from the microphone 120. When voice input is detected, the processor module 116 may automatically activate the recording module 126 to record the audio input into a voice recording file. The processor module 116 may deactivate the recording module 126 automatically when voice input is not detected for a predetermined period of time, such as, but not limited to, 5 or 10 seconds. Therefore, the recording module 126 may not record low level background noise. The processor module 116 may then store multiple voice recording files by automatically activating and deactivating the recording module 126, or may optionally store consecutive sessions of voice recordings in a single voice recording file without long time periods of silence or background noise when no voice input is present. Optionally, the processor module 116 may also activate and/or deactivate the recording module 126 based on a particular word or phrase detected from the microphone 120. For example, a particular phrase may be used, such as "start recording" and "stop recording" to activate and deactivate, respectively, the recording module 126. In this example, the operator may converse with the patient or other personnel without having unwanted conversation recorded.

An operator may not wish to record a voice recording for every image file. For example, referring to FIG. 6, the operator may scan and record a first image file 262 for Second Patient File 282. The operator may then record a second image file 264 and wish to record an associated voice recording file. The operator may record second voice recording file 266 immediately after storing the second image file 264, or simultaneously with or overlapping in time with, the second image file 264. The processor module 116 logically associates the second image file 264 and the second voice recording file 266.

In yet another embodiment, the operator may choose to store a plurality of image files, such as first, second through N image files 268, 270 and 272 in Third Patient File 284. After storing N image file 272, the operator may initiate a voice recording that is stored as N voice recording file 274. The N image file 272 and N voice recording file 274 are associated with each other. The N voice recording file 274 may refer to the N image file 272, or may provide a summary, diagnosis and/or overall findings associated with the Third Patient File 284.

Alternatively, the operator may store a plurality of image files. The operator may wish to store a voice recording file that is associated with an overall patient file rather than a specific image file. In this example, the operator may display a list of image files of a patient, and may, for example, highlight the patient identifier or a sub-folder. When the operator stores the voice recording, the voice recording file is associated with the highlighted file or folder, such as the overall patient file, rather than a specific image file.

The images may be reviewed on the ultrasound system used for acquisition and voice recording, or may be reviewed on a different system or work station. For example, images and associated voice recording(s) may be transferred over the Internet or other network, or may be transferred by way of physical media, such as disc or portable flash memory.

Figure 7:
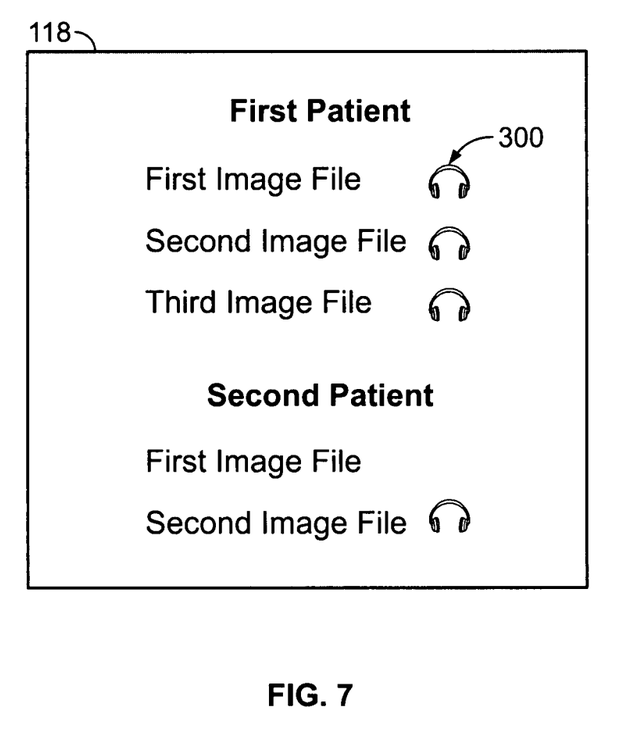
FIG. 7 illustrates a display showing a list of image files and recording icons associated therewith that may be selected and reviewed in accordance with an embodiment of the present invention.

FIG. 7 illustrates the display 118 showing a list of image files associated with first and second patients that may be selected and reviewed. When the images are reviewed, a recording icon 300 may be displayed to indicate that a voice recording associated with a particular image file from a particular patient is available. For example, the operator may select the First Patient File 280 from the list of patients. The image files within the First Patient File 280 may be displayed and selected for viewing. In this example, each of the first, second and third image files 250, 254 and 258 may have an associated recording icon 300. If the Second Patient File 282 is selected, a recording icon is not displayed associated with the first image file 262, while the second image file 264 has an associated recording icon 300. Therefore, the recording file may not be indicated as a separate file on the display 118.

In one embodiment, the voice recording may be selectable separately from the associated image file, such as by selecting the displayed recording icon 300. In another embodiment, each time an image file is selected for display, if an associated voice recording file has been stored, the voice recording is played.

Referring again to FIG. 3, in another embodiment, one or more audio recordings may be associated with an ultrasound image 190 and assigned to one or more locations in that image 190 by the operator who is being recorded. When this has been done and the image 190 is subsequently displayed, the associated recording icons 302 will be displayed on the image 190 at their assigned image locations. Hence, the operator being recorded can create one or more audio recordings (i.e. voice recording files) associated with different features of interest in the image 190 and then attach those recordings to the features they are discussing. When the image 190 with the icons 302 is subsequently displayed, the recording icons 302 are visible and can be activated (e.g. by double-clicking on them) to play the recording. The recording icons 302 can also be moved or deleted when displayed on an image 190.

A technical effect of at least one embodiment is the ability of an operator to record findings, diagnosis and the like in a hands-free manner while scanning a patient. The operator can easily activate a recording session to verbally record findings. Upon being stored in memory, the audio file, or the voice recording file, is automatically associated with a patient image file, overall patient file and/or a particular location on an image within a patient image file. Therefore, findings associated with a particular image are automatically linked or associated with the image file. The image file may be a single image frame or multiple frames, and the voice recording file may be any length, and thus an image file of multiple frames may have a different length in time than the associated image file. When a list of saved files is displayed, an icon may be used to indicate that an image file has an associated voice recording file.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. An ultrasound system, comprising:
a probe for acquiring ultrasound data associated with a patient;
a microphone for detecting audio;
a processor module configured to receive the ultrasound data from the probe, the processor module processing the ultrasound data to form an image file, the processor module being further configured to receive the audio from the microphone, the processor module forming a voice recording file based on the received audio;
a memory for storing the image, file and the voice recording file, the processor module automatically associating the image file and the voice recording file with each other; and
a display for displaying a recording icon and an image associated with the image file, wherein the recording icon indicates an ON state of recording and an OFF state of recording;
wherein the image file comprises multiple consecutive frames of data acquired over time, the processor module combining the voice recording file and the image file into a single combined file, wherein the voice recording file is synchronized with respect to the image file within the single combined file.

2. An ultrasound system, comprising:
a probe for acquiring ultrasound data associated with a patient;
a microphone for detecting audio;
a processor module configured to receive the ultrasound data from the probe, the processor module processing the ultrasound data to form an image file, the processor module being further configured to receive the audio from the microphone, the processor module forming a voice recording file based on the received audio;
a memory for storing the image file and the voice recording file, the processor module automatically associating the image file and the voice recording file with each other; and
a display for displaying a recording icon and an image associated with the image file, wherein the recording icon indicates an ON state of recording and an OFF state of recording;
wherein the recording icon is a first recording icon, the display further displaying at least one second recording icon at a first image location on the image, the ultrasound system further comprising a user interface for at least one of selecting the at least one second recording icon to play the associated voice recording file and moving the at least one second recording icon to a different image location on the image.

3. The ultrasound system of claim 2, wherein the user interface provides an audio recording control interface, the audio recording control interface being configured to provide at least one of starting a recording session and stopping a recording session.

4. The ultrasound system of claim 2, wherein the voice recording file is one of acquired subsequent to an acquisition of the image file and acquired during an acquisition of the image file.

5. The ultrasound system of claim 2, wherein the image file comprises at least one frame of data and has a length of time t1, wherein the voice recording file has a length of time t2, wherein the lengths of time t1 and t2 may be the same as each other or may be different with respect to each other.

6. The ultrasound system of claim 2, wherein the ultrasound system is one of a hand carried system, miniaturized system, pocket-sized system, and portable system.

7. The ultrasound system of claim 2, wherein the memory is configured to store recorded movements of a cursor or a visible on-screen tool while acquiring multiple consecutive frames of ultrasound data, the processor module automatically associating the image file and the recorded movements, the display being configured to display the image synchronized with the associated recorded movements and an audio output of the voice recording file.

8. The ultrasound system of claim 2, wherein the processor module automatically associates the image file and the voice recording file by storing the image file and the voice recording file in a common examination folder.

9. The ultrasound system of claim 2, wherein the processor module automatically associates the image file and the voice recording file by giving the image file and the voice recording file substantially similar names with different extensions.

10. The ultrasound system of claim 2, wherein the processor module automatically associates the image file and the voice recording file by including the same examination number into names of the image file and the voice recording file.

11. The ultrasound system of claim 2, wherein the recording icon indicates that the processor module is currently capable of recording audio.

12. The ultrasound system of claim 1, further comprising a user interface providing an audio recording control interface, the audio recording control interface being configured to provide at least one of starting a recording session and stopping a recording session.

13. The ultrasound system of claim 1, wherein the voice recording file is one of acquired subsequent to an acquisition of the image file and acquired during an acquisition of the image file.

14. The ultrasound system of claim 1, wherein the image file comprises at least one frame of data and has a length of time t1, wherein the voice recording file has a length of time t2, wherein the lengths of time t1 and t2 may be the same as each other or may be different with respect to each other.

15. The ultrasound system of claim 1, wherein the ultrasound system is one of a hand carried system, miniaturized system, pocket-sized system, and portable system.

16. The ultrasound system of claim 1, wherein the memory is configured to store recorded movements of a cursor or a visible on-screen tool while acquiring multiple consecutive frames of ultrasound data, the processor module automatically associating the image file and the recorded movements, the display being configured to display the image synchronized with the associated recorded movements and an audio output of the voice recording file.

17. The ultrasound system of claim 1, wherein the recording icon indicates that the processor module is currently capable of recording audio.

\* \* \* \* \*